United States Patent

Müller et al.

Patent Number: 4,952,701
Date of Patent: Aug. 28, 1990

[54] PREPARATION OF 4-AMINO-1,2,4-TRIAZOL-5-ONES

[75] Inventors: Klaus-Helmut Müller, Duesseldorf; Klaus König, Odenthal; Peter Heitkämper, Dormagen, all of Fed. Rep. of Germany

[73] Assignee: Bayer Aktiengesellschaft, Leverkusen, Fed. Rep. of Germany

[21] Appl. No.: 284,965

[22] Filed: Dec. 15, 1988

[30] Foreign Application Priority Data

Dec. 22, 1987 [DE] Fed. Rep. of Germany ....... 3743493
Aug. 11, 1988 [DE] Fed. Rep. of Germany ....... 3827264

[51] Int. Cl.$^5$ ............................................ C07D 249/12
[52] U.S. Cl. .................................................. 548/263.8
[58] Field of Search .......................................... 548/263

[56] References Cited

U.S. PATENT DOCUMENTS 3,884,910  5/1975  Pilgram ................................ 548/263

OTHER PUBLICATIONS

Chem. Ber. 98, 3025 [1965].
Chem. Ber. 27, 55 [1894].
J. Prakt. Chem. [2] 52, 454 [1895].
Chem. Ber. 57, 1321 [1924].
Liebigs Ann. Chem. 475, 120 [1929].
Inorganic Synthesis 4, 32 [1953].
Z. Chem. 8, 221 [1968].
Endo et al., "Syntheses and Reactions of, etc", CA 79:1056/qt (1973).
Metivier et al., "Herbicidal 3-(2,4-dichloro, etc)", CA 86: 29822f (1977).

Primary Examiner—Glennon H. Hollrah
Assistant Examiner—Patricia L. Morris
Attorney, Agent, or Firm—Sprung Horn Kramer & Woods

[57] ABSTRACT

A process for the preparation of 4-amino-1,2,4-triazol-5-one of the formula

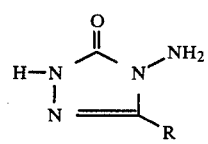

in which R is alkyl, comprising in a first step reacting phosgene with an acylhydrazide of the formula

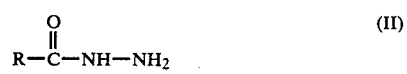

to produce an oxadiazolinone of the formula

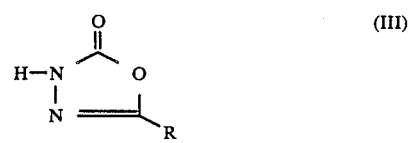

and in a second step reacting the oxadiazolinone with hydrazine hydrate.

8 Claims, No Drawings

PREPARATION OF 4-AMINO-1,2,4-TRIAZOL-5-ONES

The invention relates to a new process for the preparation of 4-amino-1,2,4-triazol-5-ones which are intermediates for the preparation of herbicidal active substances.

It is known that 4-amino-1,2,4-triazol-5-ones are obtained when carbohydrazide is thermally cyclized with carboxylic acids (cf. Chem. Ber. 98, 3025 [1965]). The disadvantage of this process is that ring closure only occurs after a relatively long reaction time (10 hours) and even self-condensation of the carbohydrazide to 4-aminourazole occurs under these reactions conditions. In this process, the yields of desired triazolone are low (16% to 22%).

Furthermore, it is known that 4-amino-1,2,4-triazol-5-ones are obtained when 1,5-diacyl-carbohydrazides are cyclized in the presence of aqueous alkali. The 1,5-diacylcarbohydrazides required for this are prepared prior to this process by warming carbohydrazide together with carboxylic acids (cf. Chem. Ber. 98, 3025 [1965]). In this process, too, the yields over both steps are not very high.

Furthermore, it is known that 4-amino-1,2,4-triazol-5-ones are obtained when $N^\beta$-acylcarbazinic acid esters are reacted with hydrazine hydrate (cf. Chem. Ber. 98, 3025 [1965]). In this process, too, the low yields are disadvantageous, in particular considering that the $N^\beta$-acylcarbazinic acid esters required as starting compounds must also first be prepared. Another serious disadvantage of this method is that only certain (3-methyl)-4-amino-1,2,4-triazol-5-ones are producible by this method. Under the same conditions, cyclization no longer occurs, even using the homologous ethyl compound ethyl $N^\beta$-propionylcarbazinate.

Furthermore, it is known that 4-amino-1,2,4-triazol-5-ones of the formula (I) described below are obtained when carbohydrazide is thermally cyclized with ortho esters (cf. Chem. Ber. 27, 55 [1894]; J. Prakt. Chem. [2]52, 454 [1895]; Chem. Ber. 57, 1321 [1924]; Liebigs Ann. Chem. 475, 120 [1929] and Inorganic Synthesis 4, 32 [1953]).

The disadvantage in this process is that ortho esters are required as starting compounds which must themselves be prepared in a multi-step synthesis, the course of which includes intermediate steps prone to hydrolysis, which results in the overall synthesis being of little advantage for economical and ecological reasons.

A further known process for the preparation of 4-amino-1,2,4-triazol-5-ones consists in the reaction of Pinner salts and carbazinic acid esters, and the subsequent cyclization with hydrazine hydrate (cf. Bull. Soc. Chim. France 1962, 1364; Eur. J. Med. Chem.—Chim. Ther. 1983, 215; Chimica Acta Turcica 7, 269 [1979]). The disadvantage in this process is the low overall yield and the preparation of the Pinner salts, for which reaction times of several days are required and which must be carried out with strict exclusion of moisture (cf. Ber. dtsch. chem. Ges. 16, 1643 [1883]; Organic Syntheses, Coll. Vol. I, 5 [1951]).

It has now been found that 4-amino-1,2,4-triazol-5-ones of the general formula (I)

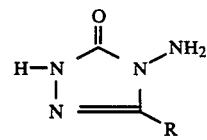

in which R stands for alkyl, are obtained when acylhydrazides of the formula (II)

in which R stands for alkyl, are reacted with phosgene, if appropriate, in the presence of a base and if appropriate in the presence of a diluent, and the resulting oxadiazolinones of the formula (III)

in which R stands for alkyl, are reacted further with hydrazine hydrate either directly in a "one-pot process" without isolation or in a separate reaction step, if appropriate in the presence of a diluent.

It must be considered extremely surprising that the reaction according to the invention yields the desired product in large amounts and in high purity, since it was known from the prior art that the ring-opening of oxadiazolinones depends largely on the substitution pattern, and the relevant 1-alkyl-3-aryl-oxadiazolinones and excess hydrazine, for example, yield aroylhydrazides only (cf. Z. Chem. 8, 221 [1968]).

It must be emphasized as an advantage of the process according to the invention that the required starting compounds of the formula (II) are inexpensive industrial products which are reacted further with very simple basic chemicals. Here, in particular the variant of the process according to the invention, in which the oxadiazolinones of the formula (III) occuring as intermediates are reacted further directly in a "one-pot process", provides a simple and cost-effective way of obtaining the desired final products in high yields and purity. Formula (I) provides a general definition of the 4-amino-1,2,4-triazol-5-ones which can be prepared with the aid of the process according to the invention.

Compounds of the formula (I) which can preferably be prepared are those in which R stands for straight-chain or branched alkyl having 1 to 8 carbon atoms.

Compounds of the formula (I) which can particularly preferably be prepared are those in which R stands for straight-chain or branched alkyl having 1 to 4 carbon atoms.

Compounds of the formula (I) which can very particularly preferably be prepared are those in which R stands for methyl or ethyl.

If, for example, acethydrazide, phosgene and hydrazine hydrate are used as starting substances, the course of the reaction of the process according to the invention may be represented by the following equation:

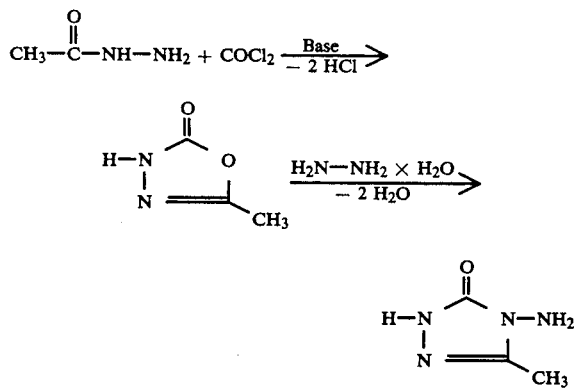

Formula (II) provides a general definition of the acylhydrazides required as starting substances for carrying out the process according to the invention. In this formula (II), R preferably stands for those radicals which have already been mentioned in connection with the description of the substances of the formula (I) according to the invention as being preferred for this substituent.

The acylhydrazides of the formula (II) are generally known compounds of organic chemistry.

The process according to the invention is preferably carried out in the presence of a suitable diluent.

Suitable diluents are inert organic solvents or aqueous systems. These include in particular aliphatic, alicyclic or aromatic, optionally halogenated hydrocarbons, such as for example benzine, benzene, toluene, xylene, chlorobenzene, petroleum ether, hexane, cyclohexane, dichloromethane, dichloroethane, chloroform, carbon tetrachloride or water.

The process according to the invention can, if appropriate, also be carried out in a two-phase system, such as, for example, water/toluene or water/dichloromethane, if appropriate in the presence of a phase transfer catalyst. The following may be mentioned as examples of such catalysts: tetrabutylammonium iodide, tetrabutylammonium bromide, tributylmethylphosphonium bromide, trimethyl-$C_{13}/C_{15}$-alkylammonium chloride, dibenzyldimethylammonium methyl sulphate, dimethyl-$C_{12}/C_{14}$-alkyl-benzylammonium chloride, tetrabutylammonium hydroxide, 15-crown-5, 18-crown-6, triethylbenzylammonium chloride, trimethylbenzylammonium chloride or tris-[2-(2-methoxyethoxy)-ethyl]-amine.

Furthermore, the first step of the process according to the invention can, if appropriate be carried out in the presence of a suitable base. Suitable bases are all customary inorganic or organic bases. These include, for example, alkali metal hydroxides, such as sodium hydroxide or potassium hydroxide, alkali metal carbonates or alkali metal hydrogen carbonates, such as sodium carbonate, potassium carbonate or sodium hydrogen carbonate, sodium carbonate or potassium carbonate being particularly preferably used as the base.

When carrying out the process according to the invention, the reaction temperatures may be varied within a relatively wide range. In general, the process is carried out at temperatures between $-20°$ C. and $+20°$ C., preferably at temperatures between $-10°$ C. and $+10°$ C. in the first step of the reaction and at temperatures between $+20°$ C. and $+120°$ C., preferably at temperatures between $+50°$ C. and $+100°$ C. in the second step of the reaction.

For carrying out the process according to the invention, 1 to 3 moles, preferably 1 to 2 moles, each of phosgene and, if appropriate base, and 1 to 10 moles, preferably 1 to 5 moles, of hydrazine hydrate are generally employed per mole of acylhydrazide of the formula (II). Here, a procedure is followed in which the acylhydrazide of the formula (II), if appropriate together with half the base are initially introduced into the diluent and phosgene is then passed in until a pH of <3 is reached, and, if appropriate, the second half of the base is then added and phosgene is again passed in until the pH is 3. When the reaction is complete, excess phosgene is removed by distillation flushing out with nitrogen, more of the diluent and an excess of hydrazine hydrate are added, and the mixture is refluxed for several hours.

The reaction products are worked up and isolated by generally customary methods. Here, it may be advantageous, if necessary, to free the resulting 4-amino-1,2,4-triazol-5-ones of the formula (I) of any adherent sodium chloride by derivatizing the former on the amino group in a customary manner, for example by converting them into azomethines using aldehydes or ketones, such as, for example, benzaldehyde or acetone, during which process any insoluble sodium chloride can easily be filtered off. The azomethine protective group can either be eliminated again from these derivatives by customary methods; however, they may also be used directly as such as starting products for further reactions.

The resulting 4-amino-1,2,4-triazol-5-ones are valuable intermediates, for example, for the synthesis of herbicidally active substances (cf., for example, U.S. Pat. No. 3,884,910 or German Patent Application No. P 3,719,575 dated June 12th, 1987).

PREPARATION EXAMPLES

Example 1

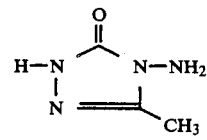

18 g (0.36 mole) of hydrazine hydrate are added to 10 g (0.1 mole) of 5-methyl-1,3,4-oxadiazol-2(3H-one in 250 ml of water, the mixture is refluxed for approximately 12 hours and evaporated to dryness, the residue is taken up in ethanol, and any insoluble product is filtered off with suction and dried.

8.2 g (72% of theory) of 4-amino-3-methyl-1,2,4-triazol-5(4H)-one of melting point 228° C. are obtained.

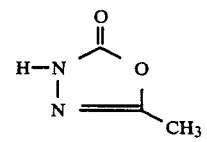

A vigorous stream of phosgene is passed into a solution of 74.0 g (1.0 mole) of acethydrazide and 53 g (0.5 mole) of anhydrous sodium carbonate in 300 ml of water, with stirring and cooling at $-5°$ C. to $+5°$ C., until the solution is weakly acid (methyl orange as indicator).

A further 53 g (0.5 mole) of sodium carbonate are then added and phosgene is passed in a second time until the indicator changes. For working up, excess phosgene is removed by flushing with nitrogen, the mixture is then extracted with ethyl acetate for 24 hours, the ethyl acetate phase is concentrated to incipient crystallization, cooled and filtered, the mother liquor is concentrated to one quarter of the volume and cooled, and a second fraction is obtained by filtration.

After drying, 80 g (80% of theory) of 2-methyl-1,3,4-oxadiazol-5(4H)-one of melting point 112° C. are obtained.

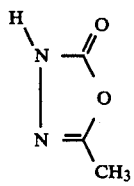

(alternative preparation)

A solution with a temperature of 50° to 60° C. of 222 g (3.0 moles) of anhydrous acethydrazide in 600 ml of anhydrous 1,2-dichloroethane is added dropwise to 450 g (4.5 moles) of phosgene in 3000 ml of anhydrous 1,2-dichloroethane at 10° C. with cooling and stirring over a period of 45 to 60 minutes. The reaction temperature of the mixture should not rise above 25° C. during this addition. When the addition has ended the mixture is heated to 40° C. to 50° C. until the evolution of gas subsides after about 60 minutes. While continuing to introduce phosgene (about 50 g per hour) the mixture is heated further to the refluxing temperature and phosgenated for 1 hour under reflux. For the working-up 1500 ml of solvent and excess phosgene are distilled off and the mixture is filtered while hot, the filtrate is concentrated and the residue is distilled in vacuo.

277 g (92% of theory) of 2-methyl-1,3,4-oxadiazol-5(4H)-one are obtained with a boiling point of 140° to 143° C. at 16 mbar and with a melting point of 110° to 111° C.

Example 2

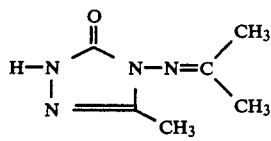

(One-pot process and conversion to azomethine)

74 g (1.0 mole) of acethydrazide, 53 g (0.5 mole) of sodium carbonate and a spatula tip of methyl orange are dissolved in 300 ml of water, and phosgene is passed in at −5° C. to +5° C. until the indicator changes. When the evolution of carbon dioxide gas has ceased, a further 53 g (0.5 mole) of sodium carbonate are added, and phosgene is again passed in until the indicator changes. After the evolution of gas has ceased, excess phosgene is removed from the solution by flushing with nitrogen, the mixture is diluted with 2.5 l of water, 180 g (3.6 moles) of hydrazine hydrate are added and the mixture is refluxed for 12 hours. After cooling, the mixture is evaporated to dryness in vacuo, the residue is stirred with ethanol and filtered, and the insoluble solid is taken up in 1.5 l of acetone, refluxed for a further 6 hours and the hot mixture is then filtered. The filtrate is concentrated and crystallized by trituration with ethanol and the crystals are filtered off with suction and dried. 99 g (64% of theory) of 4-isopropylidene-imino-3-methyl-1,2,4-triazol-5(4H)-one of melting point 138° C. are obtained.

It will be appreciated that the instant specification and claims are set forth by way of illustration and not limitation, and that various modifications and changes may be made without departing from the spirit and scope of the present invention.

What is claimed is:

1. A process for the preparation of a 4-amino-1,2,4-triazol-5-one of the formula

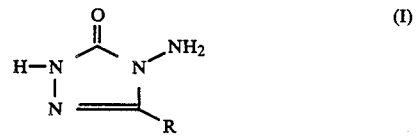

in which
R is alkyl,
comprising in a first step reacting phosgene with an acylhydrazide of the formula

to produce an oxadiazolinone of the formula

and without isolation in a second step reacting the oxadiazolinone with hydrazine hydrate.

2. A process according to claim 1, wherein the reactions are carried out in the presence of a diluent.

3. A process according to claim 2, wherein the diluent comprises benzine, benzene, toluene, xylene, chlorobenzene, petroleum ether, hexane, cyclohexane, dichloromethane, dichloroethane, chloroform, carbon tetrachloride, water or a water/toluene or water/dichloromethane mixture.

4. A process according to claim 1, wherein the first step is carried out in the presence of a base.

5. A process according to claim 4, wherein the base is an alkali metal hydroxide, alkali metal carbonate or alkali metal hydrogen carbonate.

6. A process according to claim 1, wherein the first step is carried out at a temperature between about −20° C. and +20° C.

7. A process according to claim 1, wherein about 1 to 3 moles of phosgene and about 1 to 10 moles of hydrazine hydrate are employed per mole of acylhydrazide.

8. A process according to claim 1, wherein about 1 to 2 moles of phosgene and about 1 to 5 moles of hydrazine hydrate are employed per mole of acylhydrazide.

* * * * *